(12) United States Patent
Groder et al.

(10) Patent No.: US 10,561,778 B2
(45) Date of Patent: Feb. 18, 2020

(54) SPLIT RESERVOIR BAGS AND METHOD OF USING SPLIT RESERVOIR BAGS TO IMPROVE THE HEATING AND GENERATION OF DIALYSATE

(71) Applicant: Fresenius Medical Care Holdings, Inc., Waltham, MA (US)

(72) Inventors: Seth Howard Groder, Tustin, CA (US); Barry Neil Fulkerson, Longmont, CO (US); John Arriza, Oceanside, CA (US); Nhan Viet Pham, Fountain Valley, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 414 days.

(21) Appl. No.: 15/447,519

(22) Filed: Mar. 2, 2017

(65) Prior Publication Data
US 2018/0250462 A1    Sep. 6, 2018

(51) Int. Cl.
*A61M 1/16* (2006.01)
(52) U.S. Cl.
CPC ........ *A61M 1/1668* (2014.02); *A61M 1/1664* (2014.02)
(58) Field of Classification Search
CPC ........ A61F 1/16; A61F 1/1654; A61F 1/1662; A61F 1/1664; A61F 1/1666; A61F 1/1668; A61F 1/167; A61F 1/1672; A61M 1/16; A61M 1/1654; A61M 1/1662; A61M 1/1664; A61M 1/1666; A61M 1/1668; A61M 1/167; A61M 1/1672
See application file for complete search history.

(56) References Cited

U.S. PATENT DOCUMENTS

| | | | |
|---|---|---|---|
| 3,242,456 A | 3/1966 | Duncan | |
| 3,803,913 A | 4/1974 | Tracer | |
| 3,961,918 A | 6/1976 | Johnson | |
| 3,989,625 A | 11/1976 | Mason | |

(Continued)

FOREIGN PATENT DOCUMENTS

| | | |
|---|---|---|
| DE | 19825158 C1 | 4/1999 |
| JP | 2002139165 A | 5/2002 |

(Continued)

OTHER PUBLICATIONS

International Search Report for PCT/US13/77234, dated Jun. 9, 2014.

(Continued)

*Primary Examiner* — Philip R Wiest
(74) *Attorney, Agent, or Firm* — Novel IP (57) ABSTRACT

The present specification provides a reservoir bag for containing a dialysate during a dialysis treatment. The bag has four walls and a membrane extending from a first wall to a second opposing wall which divides the bag into a first and a second sub-reservoir having changeable volumes. The maximum volume of each sub-reservoir is between 80 to 100% of the entire volume of the bag. The bag further includes at least an inlet and an outlet positioned in at least one of the walls for enabling fluid entry into and exit out of the first sub-reservoir and at least an inlet and an outlet positioned in at least one of the walls for enabling fluid entry into and exit out of the second sub-reservoir.

25 Claims, 6 Drawing Sheets

(56) References Cited

U.S. PATENT DOCUMENTS

| | | | |
|---|---|---|---|
| 4,354,562 A | 10/1982 | Newman |
| 4,397,519 A | 8/1983 | Cooney |
| 4,403,765 A | 9/1983 | Fisher |
| 4,430,098 A | 2/1984 | Bowman |
| 4,480,483 A | 11/1984 | McShane |
| 4,531,799 A | 7/1985 | Gray |
| 4,535,637 A | 8/1985 | Feller |
| 4,586,576 A | 5/1986 | Inoue |
| 4,740,755 A | 4/1988 | Ogawa |
| 4,828,543 A | 5/1989 | Weiss |
| 5,000,274 A | 3/1991 | Bullivant |
| 5,074,368 A | 12/1991 | Bullivant |
| 5,114,580 A | 5/1992 | Ahmad |
| 5,170,789 A | 12/1992 | Narayan |
| 5,228,308 A | 7/1993 | Day |
| 5,258,127 A | 11/1993 | Gsell |
| 5,725,776 A | 3/1998 | Kenley |
| 5,782,796 A | 7/1998 | Din |
| 5,808,181 A | 9/1998 | Wamsiedler |
| 5,915,932 A | 6/1999 | Nabity |
| 5,954,971 A | 9/1999 | Pages |
| 5,989,438 A | 11/1999 | Fumiyama |
| 6,044,691 A | 4/2000 | Kenley |
| 6,358,225 B1 | 3/2002 | Butterfield |
| 6,487,904 B1 | 12/2002 | Myhre |
| 6,491,656 B1 | 12/2002 | Morris |
| 6,638,478 B1 | 10/2003 | Treu |
| 6,653,841 B1 | 11/2003 | Koerdt |
| 6,681,624 B2 | 1/2004 | Furuki |
| 6,691,047 B1 | 2/2004 | Fredericks |
| 6,752,172 B2 | 6/2004 | Lauer |
| 6,836,201 B1 | 12/2004 | Devenyi |
| 6,948,697 B2 | 9/2005 | Herbert |
| 7,087,026 B2 | 8/2006 | Callister |
| 7,097,148 B2 | 8/2006 | DeWall |
| 7,270,015 B1 | 9/2007 | Feller |
| 7,387,022 B1 | 6/2008 | Korniyenko |
| 8,040,493 B2 | 10/2011 | Fulkerson |
| 8,105,487 B2 | 1/2012 | Fulkerson |
| 8,114,288 B2 | 2/2012 | Robinson |
| 8,137,553 B2 | 3/2012 | Fulkerson |
| 8,240,636 B2 | 8/2012 | Smith |
| 8,395,761 B2 | 3/2013 | Fulkerson |
| 8,475,399 B2 | 7/2013 | Fulkerson |
| 8,535,522 B2 | 9/2013 | Fulkerson |
| 8,597,505 B2 | 12/2013 | Fulkerson |
| 8,771,511 B2 | 7/2014 | Robinson |
| 9,157,786 B2 | 10/2015 | Fulkerson |
| 9,199,022 B2 | 12/2015 | Fulkerson |
| 9,201,036 B2 | 12/2015 | Fulkerson |
| 9,295,772 B2 | 3/2016 | Fulkerson |
| 9,308,307 B2 | 4/2016 | Fulkerson |
| 9,352,282 B2 | 5/2016 | Fulkerson |
| 9,354,640 B2 | 5/2016 | Byler |
| 9,358,331 B2 | 6/2016 | Fulkerson |
| 9,360,129 B2 | 6/2016 | Smith |
| 9,415,152 B2 | 8/2016 | Robinson |
| 9,517,296 B2 | 12/2016 | Fulkerson |
| 9,759,710 B2 | 9/2017 | Fulkerson |
| 2002/0151804 A1 | 10/2002 | O'Mahony |
| 2002/0158019 A1 | 10/2002 | Collins |
| 2003/0048185 A1 | 3/2003 | Citrenbaum |
| 2003/0056585 A1 | 3/2003 | Furuki |
| 2003/0220598 A1 | 11/2003 | Busby |
| 2004/0031756 A1 | 2/2004 | Suzuki |
| 2005/0086008 A1 | 4/2005 | DiGianfilippo |
| 2005/0101901 A1 | 5/2005 | Gura |
| 2005/0131332 A1 | 6/2005 | Kelly |
| 2005/0133439 A1 | 6/2005 | Blickhan |
| 2006/0195064 A1 | 8/2006 | Plahey |
| 2006/0226057 A1 | 10/2006 | Robinson |
| 2006/0289342 A1 | 12/2006 | Sugioka |
| 2007/0038191 A1* | 2/2007 | Burbank .............. A61M 1/16 604/317 |
| 2007/0112297 A1 | 5/2007 | Plahey |
| 2007/0179425 A1 | 8/2007 | Gura |
| 2007/0253463 A1 | 11/2007 | Perry |
| 2007/0269340 A1 | 11/2007 | Dannenmaier |
| 2007/0295651 A1 | 12/2007 | Martinez |
| 2008/0041792 A1 | 2/2008 | Crnkovich |
| 2008/0214979 A1 | 9/2008 | Brugger |
| 2008/0230450 A1 | 9/2008 | Burbank |
| 2008/0258735 A1 | 10/2008 | Quackenbush |
| 2008/0290974 A1 | 11/2008 | Adams |
| 2009/0008306 A1 | 1/2009 | Cicchello |
| 2009/0101549 A1 | 4/2009 | Kamen |
| 2009/0101552 A1 | 4/2009 | Fulkerson |
| 2009/0101577 A1 | 4/2009 | Fulkerson |
| 2009/0127193 A1 | 5/2009 | Updyke |
| 2010/0129247 A1 | 5/2010 | Lauer |
| 2010/0140149 A1 | 6/2010 | Fulkerson |
| 2010/0331754 A1 | 12/2010 | Fulkerson |
| 2011/0054378 A1 | 3/2011 | Fulkerson |
| 2011/0071465 A1 | 3/2011 | Wang |
| 2011/0303598 A1 | 12/2011 | Lo |
| 2011/0315611 A1 | 12/2011 | Fulkerson |
| 2012/0214117 A1 | 8/2012 | Broker |
| 2012/0310150 A1 | 12/2012 | Brandl |
| 2013/0220907 A1 | 8/2013 | Fulkerson |
| 2013/0280104 A1 | 10/2013 | Heide |
| 2014/0188040 A1 | 7/2014 | Busby |
| 2014/0276537 A1 | 9/2014 | Kruse |
| 2015/0258263 A1 | 9/2015 | Hogard |
| 2015/0314055 A1 | 11/2015 | Hogard |
| 2016/0069732 A1 | 3/2016 | Fulkerson |
| 2016/0109398 A1 | 4/2016 | Fulkerson |
| 2016/0317733 A1 | 11/2016 | Fulkerson |
| 2016/0319954 A1 | 11/2016 | Smith |
| 2017/0007756 A1 | 1/2017 | Robinson |
| 2017/0021085 A1 | 1/2017 | Fulkerson |
| 2017/0021088 A1 | 1/2017 | Fulkerson |
| 2017/0021306 A1 | 1/2017 | Fulkerson |
| 2017/0023953 A1 | 1/2017 | Byler |
| 2017/0232177 A1 | 8/2017 | Fulkerson |

FOREIGN PATENT DOCUMENTS

| | | |
|---|---|---|
| WO | 20015069412 A1 | 7/2001 |
| WO | 2009073567 | 6/2009 |
| WO | 2010042666 | 4/2010 |
| WO | 2010062698 | 6/2010 |
| WO | 2010081121 | 7/2010 |
| WO | 2012108910 | 8/2012 |
| WO | 2014105267 A1 | 7/2014 |
| WO | 2014105755 | 7/2014 |
| WO | 2014161008 | 10/2014 |
| WO | 2016172645 A1 | 10/2016 |
| WO | 2017106356 A1 | 6/2017 |

OTHER PUBLICATIONS

International Search Report for PCT/US2013/068506, dated Apr. 9, 2014.

International Search Report for PCT/US14/60122, dated Jan. 21, 2015.

International Preliminary Report on Patentability for PCT/US13/77234, dated Jun. 30, 2015.

International Search Report for PCT/US16/66671, dated Apr. 20, 2017.

International Search Report for PCT/US14/35051, dated Sep. 5, 2014.

International Search Report for PCT/US09/31228, dated Jun. 19, 2009.

International Search Report for PCT/US17/21389, dated Jun. 15, 2017.

International Search Report for PCT/US17/21456, dated Jun. 21, 2017.

International Search Report PCT/US08/85062, dated Mar. 20, 2009, XCorporeal, Inc.

International Search Report for PCT/US10/20698, Xcorporeal, Inc., dated Jun. 16, 2010.

(56) References Cited

OTHER PUBLICATIONS

International Search Report for PCT/US09/59906, Xcorporeal, Inc., dated May 8, 2012.
International Search Report for PCT/US09/62840, Xcorporeal, Inc. dated Feb. 10, 2012.
International Search Report for PCT/US11/53184, Xcorporeal, Inc., dated Mar. 2, 2012.
International Search Report for PCT/US09/59907, Xcorporeal, Inc., dated Apr. 13, 2010.
International Search Report for PCT/US10/29500, Xcorporeal, Inc., dated Jul. 2, 2010.
International Search Report for PCT/US18/19664, dated Jun. 8, 2018.

* cited by examiner

SPLIT RESERVOIR BAGS AND METHOD OF USING SPLIT RESERVOIR BAGS TO IMPROVE THE HEATING AND GENERATION OF DIALYSATE

CROSS-REFERENCE TO RELATED APPLICATIONS

The present application relates to U.S. patent application Ser. No. 14/040,362, entitled "Portable Dialysis Machine" and filed on Sep. 27, 2013 and U.S. patent application Ser. No. 14/848,012, entitled "Load Suspension and Weighing System for a Dialysis Machine Reservoir" and filed on Sep. 8, 2015, both of which are herein incorporated by reference in their entirety.

FIELD

The present specification is directed to dialysis systems with improved structural and functional features. In particular, the present specification is directed to a split reservoir bag for holding or containing a dialysate.

BACKGROUND

Blood purification systems, which are used for conducting hemodialysis, hemodiafiltration or hemofiltration, involve the extracorporeal circulation of blood through an exchanger with a semi-permeable membrane. Such systems further include a hydraulic system for circulating blood and a hydraulic system for circulating replacement fluid or dialysate comprising the certain blood electrolytes in concentrations close to that of the blood of a healthy subject. Standard dialysis treatment, using an installed apparatus in hospitals, comprises two phases, namely, (a) dialysis, in which toxic substances and scoriae (normally small molecules) pass through the semi-permeable membrane from the blood to the dialysis liquid or dialysate, and (b) ultra-filtration, in which a pressure difference between the blood circuit and the dialysate circuit, more precisely a reduced pressure in the latter circuit, causes the blood content of water to be reduced by a predetermined amount.

Conventionally, a reservoir bag is provided for storing a dialysate which comprises filtered water mixed with a patient's prescription. In certain cases, the dialysate is required to be heated to a predefined temperature (usually the patient's body temperature) before being used. The reservoir bag is usually made of a thin plastic material comprising a liner which is capable of being heated without sustaining any damage or breakdown. The bag unfolds as it fills up with the dialysate and can be heated over a hot surface or any suitable heating device used in conjunction with a dialysis system.

In order to start heating the dialysate in the bag, there needs to be enough fluid in the bag for heat transfer to take place. Conventionally, a clinician takes a 6-liter container of tap water and mixes a patient's prescription, which may be in a powder form, with the tap water. The container is then shaken to mix the water and prescription well. The container usually is provided with a top connector which is connected to a dialysis system. The fluid mixture from the container is run through a sorbent for filtration and, once treated with the sorbent, the fluid mixture/dialysate passes into the reservoir bag. A bulk of the priming procedure time comprises waiting for the reservoir bag to begin to fill. When there is enough dialysate in the bag, the dialysate begins to heat until it reaches a predefined temperature (which may be a patient's normal body temperature, i.e. 37° C.).

A problem encountered with current reservoir systems is that the reservoir bag does not sit properly in a heating pan/device, when not filled to a near full capacity, as the bag does not start "inflating" until fluid fills it up. Hence, the time spent in filling the bag is added to the time required for preparing a dialysis system. Further, the bag must be filled on site, yet be made of a material that is thin enough so that it can be heated. While, in theory, one can remove the thermoform pan and heating element with the liner and then put it back, there are still challenges with the weight of the fluid, efficiently installing the bag, and providing the bag with a proper surface to rest on.

Hence, there is a need for a reservoir bag which can be rapidly heated without having to wait for the completion of dialysate filtration. There is a need for a bag and a method of using the same which would reduce the number of steps and, hence, the time required in preparing a dialysis system for performing dialysis.

SUMMARY

The present specification discloses a reservoir bag for containing a dialysate fluid during a dialysis treatment, wherein the reservoir bag is defined at least by a first wall and a second wall and wherein the reservoir bag comprises: a membrane extending from the first wall of the reservoir bag to the second wall of the reservoir bag, said second wall opposing the first wall, wherein the membrane is attached to the first wall and the second wall so that an internal volume of the reservoir bag is divided into a first sub-reservoir and a second sub-reservoir, wherein said first sub-reservoir and second sub-reservoir are fluidically isolated from each other, wherein said membrane is flexible such that, upon application of fluid pressure, said membrane moves causing the first sub-reservoir to have a changeable volume and the second sub-reservoir to have a changeable volume, and wherein a maximum volume of the first sub-reservoir is equal to 80% to 100% of an entire amount of the internal volume of the reservoir bag and a maximum volume of the second sub-reservoir is equal to 80% to 100% of the entire amount of the internal volume of the reservoir bag; a first inlet and a first outlet positioned on a surface of the reservoir bag for enabling fluid entry into, and exit out of, the first sub-reservoir; and a second inlet and a second outlet positioned on a surface of the reservoir bag for enabling fluid entry into, and exit out of, the second sub-reservoir.

Optionally, the first wall of the reservoir bag is defined by a first length having a first midpoint positioned along said first length and said membrane has a first end attached to the first wall at said first midpoint. Optionally, the second wall of the reservoir bag is defined by a second length having a second midpoint along said second length and said membrane has a second end attached to the second wall at said second midpoint.

Optionally, the first sub-reservoir is adapted to receive an unfiltered mixture of water and compounds via the first inlet and adapted to be a source of said unfiltered mixture of water and compounds to a sorbent device in a dialysis machine via the first outlet. Optionally, the second sub-reservoir is adapted to receive a filtered mixture of water and compounds via the second inlet and adapted to be a source of said filtered mixture of water and compounds to the dialysis machine via the second outlet.

The may have a thickness that is less than a thickness of said first wall and said second wall.

The reservoir bag may comprise one or more handles extending outside the bag for moving the bag.

Optionally, the first wall of the reservoir bag is defined by a first length having a first midpoint positioned along said first length and a first end of the membrane is attached to the first wall at a location along the first wall that is positioned at a distance less than the distance to the first midpoint.

Optionally, the second wall of the reservoir bag is defined by a second length having a second midpoint positioned along said second length and a second end of the membrane is attached to the second wall at a location along the second wall that is positioned at a distance less than the distance to the second midpoint.

Optionally, the reservoir bag further comprises a third inlet positioned on a surface of the reservoir bag for enabling fluid entry into, and exit out of, the first sub-reservoir.

The present specification also discloses a method of heating water in a reservoir bag to be used in a dialysis treatment, the reservoir bag comprising a first sub-reservoir and a second sub-reservoir, wherein the first and second sub-reservoirs are fluidically isolated, the method comprising: filling the first sub-reservoir with unfiltered water through a first inlet on said reservoir bag; applying heat to the reservoir bag to heat up the unfiltered water in said reservoir bag to a predefined temperature; extracting the unfiltered water out of the first sub-reservoir through a first outlet; passing the unfiltered water through a sorbent cartridge to generate filtered water; filling the filtered water into the second sub-reservoir through a second inlet; determining a temperature of the filtered water in the reservoir bag; and terminating heating the reservoir bag when the filtered water has a predefined temperature.

Optionally, the method further comprises adding a plurality of compounds to the unfiltered water through the first inlet.

Optionally, the reservoir bag comprises a membrane extending from a first wall of the reservoir bag to a second opposing wall of the reservoir bag, wherein the membrane is attached to the first wall and the second wall so that an internal volume of the reservoir bag is divided into the first sub-reservoir and the second sub-reservoir. The membrane may be flexible such that, upon application of fluid pressure, said membrane moves causing the first sub-reservoir to have a changeable volume and the second sub-reservoir to have a changeable volume. Optionally, a maximum volume of the first sub-reservoir is equal to 80-100% of the internal volume of the reservoir bag and a maximum volume of the second sub-reservoir is equal to 80-100% of the internal volume of the reservoir bag. Optionally, the first inlet and the first outlet are positioned on a surface of the reservoir bag for enabling fluid entry into, and exit out of, the first sub-reservoir and the second inlet is positioned on a surface of the reservoir bag for enabling fluid entry into, and exit out of, the second sub-reservoir.

Optionally, when said dialysis treatment is initiated, the first sub-reservoir contains a first volume of fluid and the second sub-reservoir comprises an amount of fluid equal to 0 to 10% of the first volume of fluid. Optionally, after a priming procedure, the first sub-reservoir contains 10-40% of the first volume of fluid and the second sub-reservoir comprises between 20-70% of the first volume of fluid.

Optionally, the method further comprises periodically performing a plurality of dilutions during said dialysis treatment by passing water from the first sub-reservoir to the second sub-reservoir. Optionally, after a first dilution of said plurality of dilutions, the first sub-reservoir contains 5-35% of the first volume of fluid and the second sub-reservoir comprises between 40-80% of the first volume of fluid. Optionally, after a second dilution of said plurality of dilutions, the first sub-reservoir contains 0-30% of the first volume of fluid and the second sub-reservoir comprises between 50-90% of the first volume of fluid. Optionally, after a third dilution of said plurality of dilutions, the first sub-reservoir contains 0-25% of the first volume of fluid and the second sub-reservoir comprises between 60-100% of the first volume of fluid. Optionally, after a fourth dilution of said plurality of dilutions, the first sub-reservoir contains 0-15% of the first volume of fluid and the second sub-reservoir comprises between 70-110% of the first volume of fluid. Optionally, after a fifth dilution of said plurality of dilutions, the first sub-reservoir contains 0-15% of the first volume of fluid and the second sub-reservoir comprises between 80-120% of the first volume of fluid. Optionally, after a sixth dilution of said plurality of dilutions, the first sub-reservoir contains 0-10% of the first volume of fluid and the second sub-reservoir comprises between 90-130% of the first volume of fluid. Optionally, at an end of the dialysis treatment, the first sub-reservoir contains 0-10% of the first volume of fluid and the second sub-reservoir comprises between 100-140% of the first volume of fluid.

The aforementioned and other embodiments of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

While the present specification may be embodied in many different forms, for the purpose of promoting an understanding of the principles of the specification, reference will now be made to the embodiments illustrated in the drawings and specific language will be used to describe the same. It will nevertheless be understood that no limitation of the scope of the specification is thereby intended. Any alterations and further modifications in the described embodiments, and any further applications of the principles of the specification as described herein are contemplated as would normally occur to one skilled in the art to which the specification relates.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present specification is directed towards multiple embodiments. The following disclosure is provided to enable a person having ordinary skill in the art to practice the invention. The language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications, and equivalents consistent with the principles and features disclosed. For the purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

Figure 1:
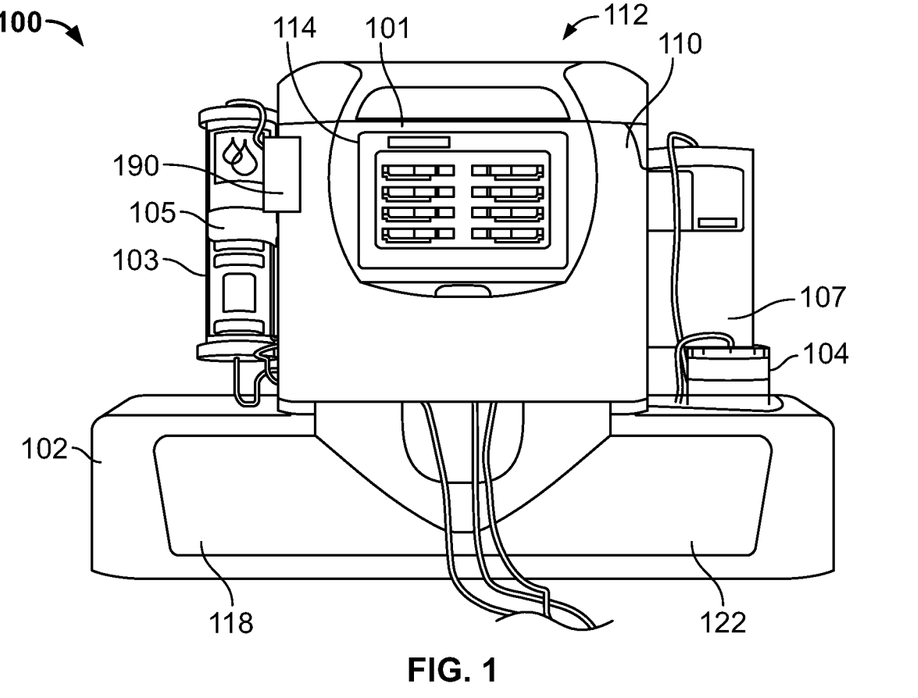
FIG. 1 is a front view of a dialysis system.
Figure 2:
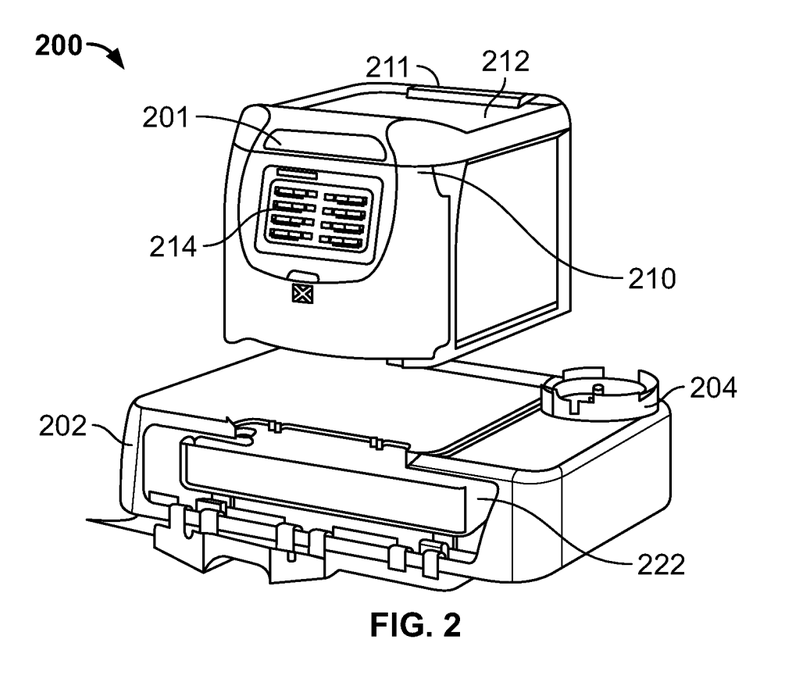
FIG. 2 is a perspective view of the dialysis system of FIG. 1.

FIG. 1 and FIG. 2 illustrate front and perspective views respectively, of a dialysis system 100, 200 in conjunction with which the dialysate reservoir bag of the present specification may be used. It would be apparent that the dialysis system 100, 200 shown in FIG. 1 and FIG. 2 is merely exemplary and that the dialysate reservoir bag of the present specification may be used with any dialysis system comprising a heating mechanism for heating the bag. Referring to FIGS. 1 and 2, the dialysis system 100, 200 comprises a top unit 101, 201 that is detachably affixed to a base element 102, 202. The base element 102, 202 comprises a reservoir 122, 222 for fluid storage, measurement, and monitoring. The top unit 101, 201, also referred to as the main unit or controller unit, comprises a graphical user interface 114, 214, pumping unit, and a door 110, 210 with a power lock and mechanical backup mechanism, as further discussed below.

To a first side of the top unit 101, 201 is a clasp 105 used to detachably affix a dialyzer 103. To a second, opposing side of the top unit 101, 201 is a sorbent cartridge locking base 104, 204 used to detachably affix a sorbent cartridge 107. It should be appreciated that in other embodiments, the clasp, hemofilter, sorbent cartridge locking base, and sorbent cartridge can be positioned on the same side of the top unit. In either case, the bottom unit has a sufficiently larger area relative to the top unit such that shelves are formed on either side of the top unit to hold the sorbent cartridge, to hold an infusate jar, to capture any spillage, and/or to channel any leaks into a leak detector.

Between the dialyzer 103 and door 110 are anti-coagulant pumps in the form of syringe pumps 190. Optionally, the top unit 101 can comprise a bottle holder that has a spiked base to receive a bottle, top-down, within the bottle holder housing. Infusion lines are connected to the inlet of the blood pump, outlet of the blood pump, or outlet of the dialyzer (blood side). The infusion lines could also 'thread' through air bubble detectors to sense if/when the anti-coagulant is emptied or blocked.

Atop the top unit 201 are the handles 211 and a workspace in the form of a useable shelf 112, 212. The handles, located on the upper pumping portion of the system, are directly connected to the internal structure or frame of the system and are not simply an extension of the exterior plastic molding, housing, or skins surrounding the top unit 101, 201. The direct connection to the internal frame of the system permits using the handle to reposition the system in a manner that is safe and can reliably handle the load, particularly when the instrument is in operation with six liters of water (adding approximately 40 lbs).

The base element 102 has a door 118 which, when pulled and not blocked by any protrusion, slides the reservoir 122 out, or otherwise makes the reservoir 122 accessible to a user, to allow a user to insert or change fluids used for dialysis. The reservoir volume is monitored by a scale system. The scale-based fluid balance is integrally formed with the reservoir and provides accurate fluid removal data and enables accurate balance calculations, thereby preventing hypotension and other ailments caused by fluid imbalances.

Figure 3:
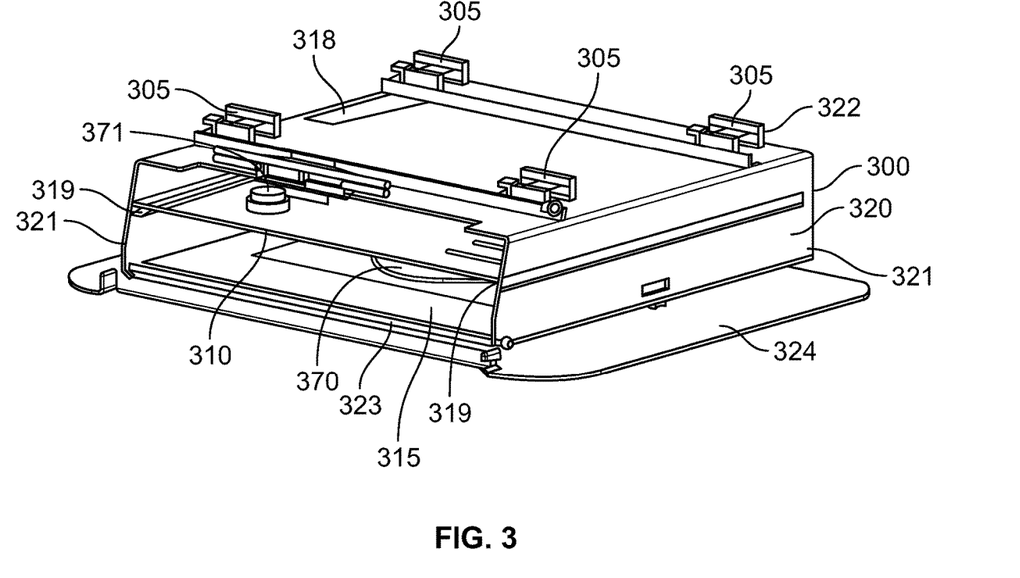
FIG. 3 is a schematic view of an internal structure of a reservoir unit of the dialysis system of FIG. 1.

Referring to FIG. 3, the reservoir internal structure 300 of a reservoir system, which may be used for heating a dialysate reservoir bag of the present specification, is shown. A metallic internal frame 320 comprises two sides 321, a back 322, an open-faced front 323, and a base 324. The internal structure or frame is shown without the external housing, as depicted as base element 102 in FIG. 1. A scale surface 318 is integrated into the reservoir internal structure 300. The bottom surface 315 of the scale surface 318 comprises a metal surface or pan that, together with the rest of the scale surface 318, is suspended from the external reservoir housing (shown as base element 102 in FIG. 1) by four flexures 305. Below the bottom surface 315 of the scale is preferably situated a heating pad, such as a square, rectangular, circular, or other shaped surfaces capable of incurring a temperature increase and conducting the increased temperature, as heat, to surface 315. A conductivity coil 370, capable of exerting a field and using changes in that field to measure conductivity, is integrated into the bottom surface 315. Accordingly, when a reservoir bag (not shown) is placed on bottom surface 315, it can be heated by a heating pad and, because it is in contact with coil 370, its conductivity can be monitored. In an embodiment of the present specification, a mark may be provided on an external surface of the reservoir or the pan indicating a position of placement of the reservoir bag, thereby enabling a user to place the reservoir bag in the reservoir correctly.

The internal surfaces of the sides 321 comprise a plurality of rails, elongated members, or protrusions 319 that serve to secure, hold, encase or attach to a disposable reservoir bag mounting surface, such as a plastic sheet, 310 to which a reservoir bag can be attached. Specifically, a reservoir bag positioned on surface 315 can have an outlet attached to conduit 371 integrated into sheet 310. Mounted in each of the four corners of the scale surface 318 are flexures 305 with each one comprising a hall sensor and a magnet.

Figure 4A:
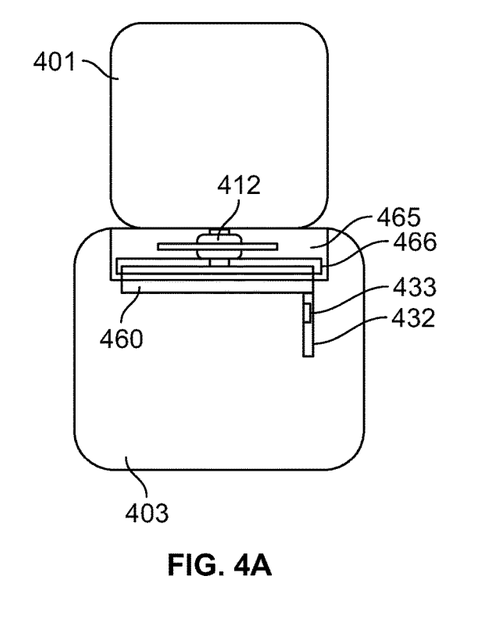
FIG. 4A is a front view illustration of one embodiment of a dialysis machine that can be used in conjunction with a dialysis reservoir bag of the present specification.
Figure 4B:
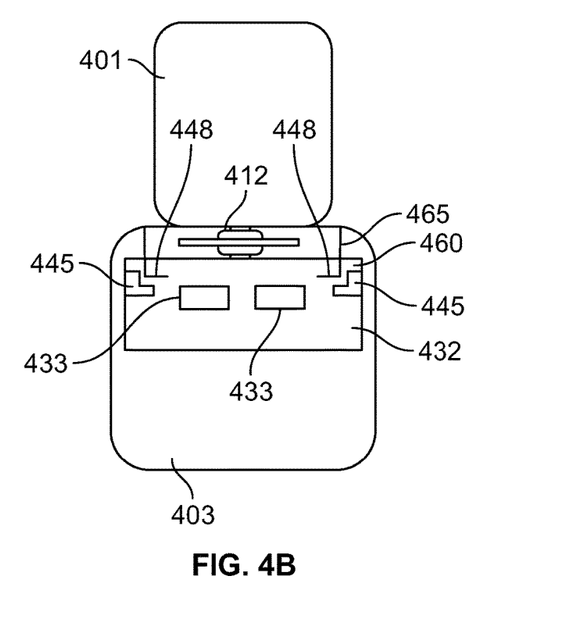
FIG. 4B is a side view illustration of one embodiment of the dialysis machine of FIG. 4A.

FIG. 4A is a front view illustration of one embodiment of a dialysis machine, that can be used in conjunction with a dialysis reservoir bag of the present specification and FIG. 4B is a side view illustration of the dialysis machine of FIG. 4A. FIGS. 4A and 4B depict a flexure assembly 412 and first 460 and second 465 internal frames therein. The front and sides of the dialysis machine have been made transparent, and the reservoir unit has been removed to enhance visualization. The dialysis machine comprises top 401 and bottom section 403 sections. In one embodiment, the bottom section 403 houses the flexure assembly 412 and associated components. The second internal frame 465 is attached to the bottom surface of a top portion of a frame that defines the housing of the bottom section 403 of the dialysis machine. The second internal frame 465 includes a top plate, two side walls with openings 466 for passage of the top plate of the first internal frame 460, and a pair of horizontal tracks 448. In one embodiment, the horizontal tracks 448 of the second internal frame 465 extend along the front to back axis of the dialysis machine, from a point proximate the front of the machine to a point proximate the back of the machine.

The flexure assembly 412 is attached to the bottom surface of a top portion of a frame that defines the housing of the bottom section 403 of the dialysis machine. In one embodiment, a top plate of the first internal frame 460 connects to the bottom of the flexure assembly 412. The first internal frame includes a top plate, two sides with horizontal tracks 445, and a back plate 432 with electrical contact elements 433. In one embodiment, the horizontal tracks 445 of the first internal frame 460 extend along the front to back axis of the dialysis machine, from a point proximate the front of the machine to a point proximate the back of the machine. In one embodiment, the back plate 432 is rectangular shaped and includes the electrical contact elements 433 which align with and contact the electrical contact plate on the insertion side of the reservoir unit. The first internal frame 460 includes a pair of tracks 445, with one track extending along each side of the dialysis machine. Each track 445 is connected to the back plate 432 at its back end. When inserted, the reservoir unit is suspended on the tracks 445 of the first internal frame 460.

The three hall sensor pairs of the flexure assembly are fixed in a static magnetic field. When the assembly is used to measure the contents of the reservoir, the magnetic field moves on the vertical axis and this movement is used to calculate the weight of the reservoir contents. Before a weight is applied, the assembly is calibrated with a voltage output of zero. The magnetic fields of the upper and lower magnets repel each other and create a centerline zero magnetic plane. The pole orientation of the magnets insures an increasing voltage output as weight is applied and the magnets move in relation to the hall sensors. A processor on the circuit board translates the change in voltage into a weight measurement using a function of the voltage. It should be appreciated that the weight is a function of voltage changes and can be experimentally derived by plotting different weights against different voltage levels and/or voltage changes. That experimentally derived plotting will yield an implementable function that relates a measured voltage level or measured voltage change against weight values, thereby allowing a processor to accurately calculate a weight from an inputted voltage level or voltage change.

In one embodiment, the hall sensors output an analog signal proportional to the change in voltage. The output is converted by an analog to digital converter (ADC) into a digital output to obtain a higher resolution. In one embodiment, the weight, in grams, of the contents of the reservoir unit is calculated using the following equation:

$$\text{Weight} = w3 + w2 + w1 + w0 \quad \text{[EQUATION 1]}$$

wherein, $w0 = k0$;
$w1 = k1 * \text{ADC}$ value (in milliVolts) of the hall sensor (Hall);
$w2 = k2 * \text{ADC}$ voltage reference (Vref) value; and,
$w3 = k3 * \text{ADC}(\text{Hall}) * \text{ADC}(\text{Vref})$ k0 through k3 represent constants and, in various embodiments, have the following values: $k0 = -7925.4 +/- 0.10$; $k1 = 328.741\text{e-}3 +/- 1.0\text{e-}6$; $k2 = -73.688\text{e-}3 +/- 1.0\text{e-}6$; and, $k3 = 935.35\text{e-}9 +/- 10\text{e-}12$.

Figure 5A:
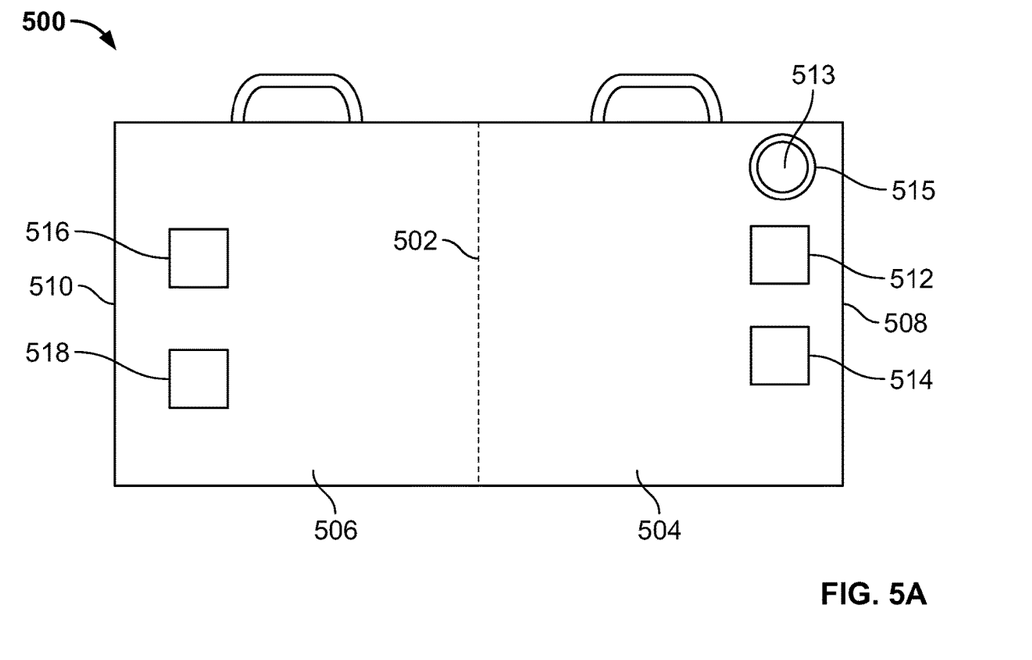
FIG. 5A illustrates a top view of a diagrammatic representation of a dialysis reservoir bag, in accordance with an embodiment of the present specification.

FIG. 5A illustrates a top view of a diagrammatic representation of a dialysis reservoir bag, in accordance with an embodiment of the present specification. Bag 500 comprises a movable membrane 502 which divides an internal volume of the bag 500 into a first sub-reservoir 504 and a second sub-reservoir 506. Membrane 502 may be moved between a first end 508 and a second end 510 of the bag 500, for increasing or decreasing the volumes of the sub-reservoirs 504, 506 as per requirement. In an embodiment, the membrane 502 moves due to application of fluid pressure exerted by fluid filled into the bag 500 making the internal volume of a sub-reservoir bigger or smaller. In an embodiment, the bag 500 comprises one or more handles 503 for manipulating the bag 500 to fill the first sub-reservoir 504 with water and/or to move the bag 500 onto a heating element.

Bag 500 further comprises a first inlet 512 and a first outlet 514 positioned so as to serve as inlet and outlet for first sub-reservoir 504, and a second inlet 516 and a second outlet 518 positioned so as to serve as inlet and outlet for second sub-reservoir 506. In various embodiments, an unfiltered mixture, for example, tap water, alone or mixed with a patient's dialysis prescription, is filled into the first sub-reservoir 504 via first inlet 512. The tap water, with or without the patient's dialysis prescription, is then passed over a sorbent device external to the bag 500 via first outlet 514 for filtration. After passing over the sorbent, the filtered mixture or liquid, also termed as dialysate fluid, is filled into second sub-reservoir 506 via second inlet 516. Heated dialysate fluid then flows through outlet 518 for dialysis. Hence, the bag 500 is filled to a sufficiently full capacity at all times, making a base of the bag 500 stable for being positioned upon a heating device, which is configured to heat the dialysate fluid filled in the bag 500 to the desired temperature. In some embodiments, the flow path can be reversed as needed.

In an embodiment, during filtering of the tap water to create dialysate, approximately 2 liters of fluid flows out of the first sub-reservoir, passes over the sorbent and flows into the second sub-reservoir at a time, thereby ensuring that the bag 500 contains, between the two sub-reservoirs, at least 4 liters of fluid at any time. In another embodiment, the total amount of fluid in the two sub-reservoirs is in a range of 3 to 5 liters at any given time, preferably 3.5 to 4.5 liters at any given time, and more preferably 3.8 liters to 4.2 liters at any given time. This ensures that the surface area of a base of the bag 500 placed on a heating device is large enough to cause quick and even heating of the fluid. Use of the bag 500 also combines the fluid preparation step (mixing a patient's prescription with unfiltered water and then filtering the same by running over a sorbent) and the fluid heating step, thereby reducing treatment preparation time.

It should be appreciated that, in operation, the amount of fluid leaving the first sub-reservoir is balanced by the amount of fluid entering the second sub-reservoir. Accordingly, during at least some portion of the operation, the rate of fluid flow out of the first sub-reservoir is approximately equal to, or at least within 10% of, the rate of fluid flow into the second sub-reservoir. Additionally, during at least some portion of the operation, the mass of fluid lost by the first sub-reservoir during a given period is equal to the mass of fluid gained by the second sub-reservoir during that same period.

In another embodiment, the first sub-reservoir 504 is configured to accommodate the volume of water necessary for treatment, which, in an embodiment is 6 liters, combined with a prescription, which in an embodiment is 3 liters, for a total of 9 liters. The capacity of the first sub-reservoir 504 ranges between 9 liters and 12 liters. The second sub-reservoir 506 is of sufficient size to accommodate the 9 liters of water and prescription mixture from the first sub-reservoir 504 (minus the mixture passing through the sorbent cartridge at a given instant, which is approximately 2 liters) as well as fluids removed from a patient's body, which in an embodiment is 4 liters, and electrolyte fluids which in an embodiment is approximately 3 liters. Hence, in embodiments, the capacity of sub-reservoir 506 ranges between 11 and 13 liters, and, preferably, is 12 liters. In an embodiment, a maximum volume of each of the first and second sub-reservoirs 504, 506 ranges from 80% to 100% of an entire amount/total of the internal volume of the reservoir bag 500.

Because both the filtered and unfiltered water filled in the two sub-reservoirs 504, 506 are heated simultaneously, treatment preparation time and complexity are reduced. In various embodiments, the required temperature and the amount of heat required to be transferred to the fluid in the bag 500 is determined using the patient's prescription and fluid weight.

In an embodiment, one or more of the inlets and outlets 512, 514, 516 and 518 may be coupled with an external pump for diluting the fluid in the bag 500 as required. In an embodiment, the first inlet 512 is a conduit through which unfiltered tap water is pumped into the first sub-reservoir 504, while a third inlet 513 corresponding to the same first sub-reservoir 504 is a conduit through which prescription powder can be added to the water. In another embodiment, the prescription is added to the water via the first inlet 512 and the third inlet 513 is not included.

Figure 5B:
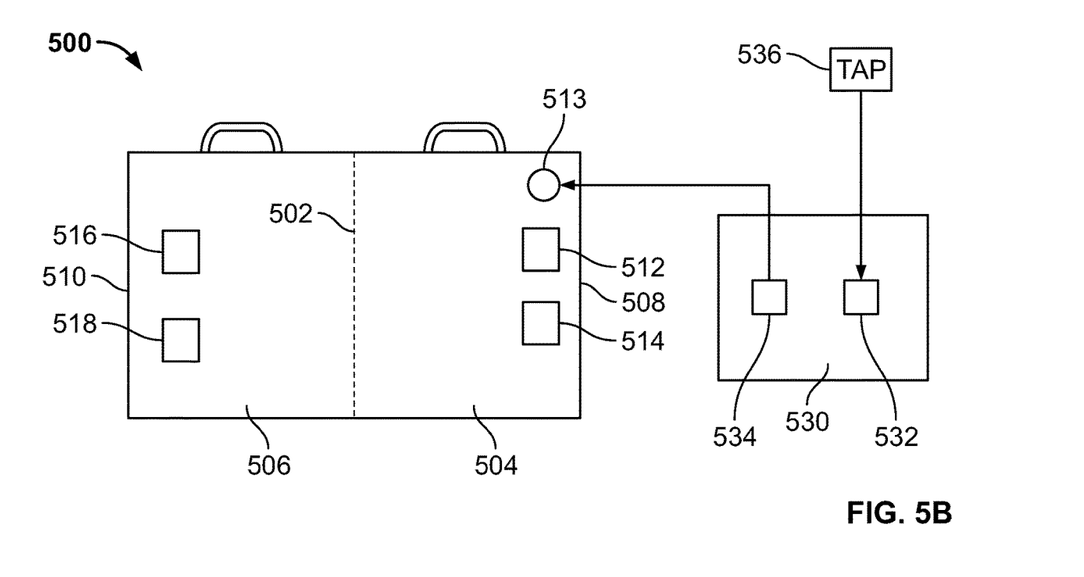
FIG. 5B illustrates a top view of an exemplary prescription bag that may be used with the reservoir bag, in an embodiment of the present specification.

In some embodiments, the prescription is added to the bag 500 in the form of a prescription bag threaded onto the first inlet port 512 or third inlet port 513. FIG. 5B illustrates a top view of an exemplary prescription bag that may be used with the reservoir bag, in an embodiment of the present specification. In an embodiment, the prescription bag is a container 530 comprising an inlet 532 and an outlet 534. The outlet 534 of the container 530 is coupled to either the first inlet port 512 or third inlet port 513 (as shown in FIG. 5B) of the bag 500, and the inlet 532 of the container 530 is coupled to a water source 536. A predefined quantity of water is filled into the container 530 via the inlet 532 to dilute the prescription contained in the container 530, which diluted prescription then passes into the bag 500 via the outlet of the container 530 coupled to either the first inlet port 512 or third inlet port 513. In other embodiments, the prescription is added to the bag 500 in the form of a prescription pod dropped into the first sub-reservoir 504 through the first inlet port 512 or third inlet port 513. In an embodiment, the third inlet 513 for adding the prescription to the bag 500 is larger than the remaining inlet and outlets of the bag and is provided with a screw-on cap 515.

Figure 6A:
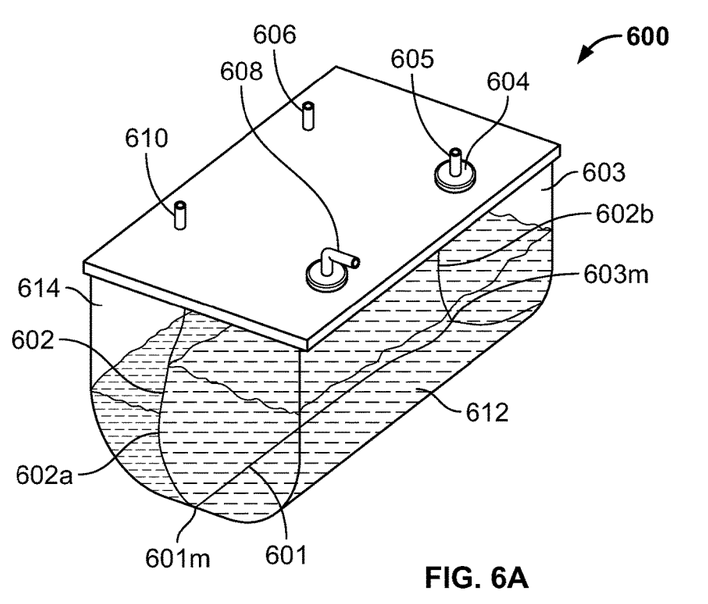
FIG. 6A illustrates a perspective view of a dialysis reservoir bag, in accordance with an embodiment of the present specification.

FIG. 6A illustrates a perspective view of a dialysis reservoir bag 600, in accordance with another embodiment of the present specification. The reservoir bag 600 comprises a movable membrane 602 dividing the reservoir bag 600 into a first sub-reservoir 612 and a second sub-reservoir 614. First inlet 604 and first outlet 608 are in fluid communication with first sub-reservoir 612 and second inlet 606 and second outlet 610 are in fluid communication with second sub-reservoir 614. The volumes of the sub-reservoirs 612, 614 are dynamic as the movable membrane 602 moves to accommodate incoming fluid into the reservoir bag 600. In an embodiment, the movable membrane 602 is made of a plastic material which is the same material used for fabricating the reservoir bag 600. In another embodiment, the movable membrane 602 is made of any material that is pliable, flexible and can transfer heat. In an embodiment, the thickness of the movable membrane 602 is less than the thickness of the walls of the reservoir bag 600. In an embodiment, the top and bottom ends of the movable membrane 602 are fixed to the top and bottom walls of the reservoir bag 600, respectively; while a middle portion of the movable membrane 602 stretches and bows towards the first sub-reservoir 612 or the second sub-reservoir 614 depending upon which sub-reservoir holds a greater volume of fluid.

In an embodiment, the membrane is attached at a location on at least one wall of the reservoir 600, such that the location is at a midpoint positioned along the length of the reservoir wall. In an embodiment, a first end 602a of the membrane 602 is attached at a location on a first wall 601 of the reservoir 600, such that the location is at a first midpoint 601m positioned along the length of the reservoir wall 601. In an embodiment, the a second end 602b of the membrane 602, opposite said first end 602a, is attached at a location on a second wall 603 of the reservoir 600, such that the location is at a second midpoint 603m positioned along the length of the reservoir wall 603. In other embodiments, the first end of the membrane is attached to the first wall at a location along the first wall that is positioned at a distance less than the distance to the first midpoint, and the second end of the membrane is attached to the second wall at a location along the second wall that is positioned at a distance less than the distance to the second midpoint, to create sub-reservoirs having unequal volumes.

In an embodiment, the movable membrane 602 is affixed in the center of the reservoir bag 600 dividing the bag into two equal halves in an un-stretched state. In another embodiment, the movable membrane 602 is affixed in an offset manner, such that the first sub-reservoir 612 is smaller in volume than the second sub-reservoir 614. In yet another embodiment, the movable membrane 602 is affixed in an offset manner, such that the first sub-reservoir 612 is larger in volume than the second sub-reservoir 614. In an embodiment, the dimensions of the movable membrane 602 in a stretched state are such that movable membrane 602 is capable of bowing completely toward one side wall of the reservoir bag 600 making the volume of one of the sub-reservoirs near zero. In various embodiments, the movable membrane 602 is placed at a predefined location within the reservoir bag 600 such that the placement minimizes the flexibility requirement of the membrane 602 by not causing the membrane 602 to stretch too far on either side.

In embodiments, unfiltered water, with or without prescription powder (in any form, such as pods or bags) is filled into first sub-reservoir 612 of reservoir bag 600 via first inlet 604. In an embodiment, first inlet 604 is wider than second inlet 606 and comprises a cap 605 for closing the same in a leak proof manner. In an embodiment, first inlet 604 is used for filling the first sub-reservoir 612 with tap water, with or without inserting prescription pods or bags, while second inlet 606 is used for filling the second sub-reservoir 614 of the reservoir bag 600 with filtered mixture of water and predefined chemicals which has been drawn from said first sub-reservoir 612 through outlet 608 and passed through a sorbent. The first outlet 608, the second inlet 606 as well as the outlet 610 are operated/controlled via one or more pumps. When the first sub-reservoir 612 of the reservoir bag 600 is filled with tap water with or without prescribed compounds, movable membrane 602 moves accordingly to accommodate the fluid. The liquid is then made to flow through a sorbent (placed external to the reservoir bag 600) via first outlet 608 for filtration, and the filtered mixture then flows into the second sub-reservoir 614 through second inlet 606. The movable membrane 602 moves as the incoming fluid flows into the second sub-reservoir 614. Heated dialysate then flows through outlet 610 for dialysis.

During the course of the dialysis process, the mixture from the second sub-reservoir 614 is cycled through a dialyzer at a rate of approximately 300 mL/minute, and back to the second sub-reservoir 614, thereby changing the chemical composition of the mixture in the second sub-reservoir 614 as quantities of urea from the patient undergoing the dialysis treatment as well as other chemicals from the dialyzer are added to the second sub-reservoir 614. Hence, the mixture in the second sub-reservoir 614 requires periodic or continuous dilution by addition of water obtained from the first sub-reservoir 612.

In an embodiment, at the beginning of the dialysis process, 9 liters of tap water is filled in the first sub-reservoir 612 while the second sub-reservoir 614 is empty. As the treatment progresses, the water from the first sub-reservoir 612 is passed over a sorbent for filtration and initially, approximately, 6 liters of filtered water is filled into the second sub-reservoir 614 and is mixed with the patient's prescription therein to form the dialysate, while approximately 2 liters of tap water runs through the sorbent. In an embodiment, filtered water is pumped into the second sub-reservoir 614 at a rate of approximately 200 mL/minute. Since the reservoir bag 600 in its entirety contains approximately 9 liters of fluid at any given time, the priming procedure of the dialysate (heating to a required temperature) commences along with (simultaneously) filling of water in the reservoir bag 600.

In an embodiment, during the dialysis process, periodic dilution occurs at 30 minute intervals, whereby a total of approximately 500 mL of the tap water from the first sub-reservoir 612 is moved through the sorbent into the second sub-reservoir 614, to dilute the dialysate in the second sub-reservoir 614. At the end of the process, the first sub-reservoir 612 is emptied, while the second sub-reservoir 614 contains approximately 12 liters of fluid which can then be discarded. In another embodiment, the dilution process is continuous whereby water is continually transferred from the first sub-reservoir to the second sub-reservoir.

Table 1 below illustrates the amount of dialysate contained in the second sub-reservoir 614 and the amount of tap water contained in the first sub-reservoir 612 at various stages during an exemplary dialysis process with a treatment time of 4 hours and a 4 L treatment goal. It should be appreciated that the numbers below represent exemplary figures and that the present invention is directed to amounts that are in within 30% of the numbers provided below and any numerical increment therein.

|  | Dialysate in second sub-reservoir (liters) | Tap water in first sub-reservoir (liters) |
| --- | --- | --- |
| Start of Dialysis | 0 | 9 |
| After Prime | 4 | 3 |
| After $1^{st}$ dilution | 5.5 | 2.5 |
| After $2^{nd}$ dilution | 6.6 | 2 |
| After $3^{rd}$ dilution | 7.6 | 1.5 |
| After 4th dilution | 8.7 | 1 |
| After 5th dilution | 9.7 | 0.5 |
| After 6th dilution | 10.8 | 0 |
| End of treatment | 11.3 | 0 |

Accordingly, at the start of operation the first sub-reservoir contains a first volume of fluid and the second sub-reservoir comprises little or no fluid, i.e. less than 10% of the first volume. After completion of the priming procedure, the first sub-reservoir contains 10-40% of the first volume of fluid and the second sub-reservoir comprises between 20-70% of the first volume of fluid. In some embodiments, a plurality of dilutions are performed during the dialysis treatment by passing water from the first sub-reservoir to the second sub-reservoir. After a first dilution, the first sub-reservoir contains 5-35% of the first volume of fluid and the second sub-reservoir comprises between 40-80% of the first volume of fluid. After a second dilution, the first sub-reservoir contains 0-30% of the first volume of fluid and the second sub-reservoir comprises between 50-90% of the first volume of fluid. After a third dilution, the first sub-reservoir contains 0-25% of the first volume of fluid and the second sub-reservoir comprises between 60-100% of the first volume of fluid. After a fourth dilution, the first sub-reservoir contains 0-15% of the first volume of fluid and the second sub-reservoir comprises between 70-110% of the first volume of fluid. After a fifth dilution, the first sub-reservoir contains 0-15% of the first volume of fluid and the second sub-reservoir comprises between 80-120% of the first volume of fluid. After a sixth dilution, the first sub-reservoir contains 0-10% of the first volume of fluid and the second sub-reservoir comprises between 90-130% of the first volume of fluid. At the end of treatment, the first sub-reservoir contains 0-10% of the first volume of fluid and the second sub-reservoir comprises between 100-140% of the first volume of fluid.

Figure 6B:
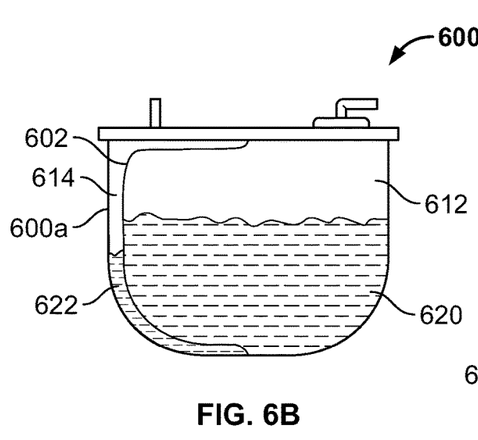
FIG. 6B illustrates a front view of the dialysis reservoir shown in FIG. 6A.
Figure 6C:
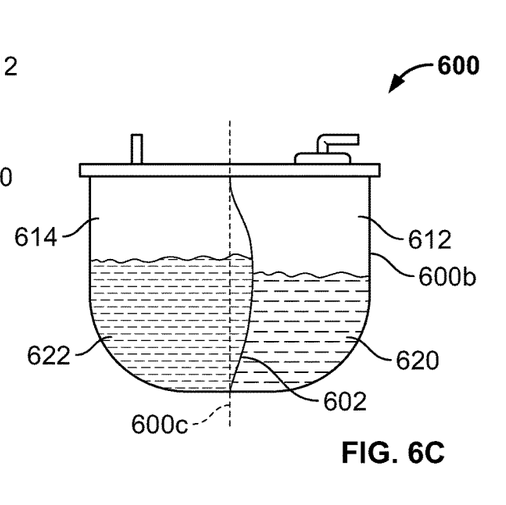
FIG. 6C illustrates another front view of the dialysis reservoir shown in FIG. 6A.

FIG. 6B illustrates a front view of the dialysis reservoir the reservoir bag 600 shown in FIG. 6A. The reservoir bag 600 is depicted in FIG. 6B before priming or filtering of tap water into the dialysate. As shown, the reservoir bag 600 is almost full with unfiltered water 620, with or without prescribed components, in the first sub-reservoir 612, while very little filtered dialysate 622 is present in the second sub-reservoir 614. Movable membrane 602 is positioned proximate a first side 600a of the reservoir bag 600 to accommodate the unfiltered water 620. FIG. 6C illustrates another front view of the dialysis reservoir bag 600 shown in FIG. 6A. The reservoir bag 600 is depicted in FIG. 6C after priming or filtering of tap water into the dialysate. As shown, reservoir bag 600 is filled with less unfiltered water 620, with or without prescribed components, in the first sub-reservoir 612, and more filtered dialysate 622, in the second sub-reservoir 614, relative to the volumes shown in FIG. 6B. In an embodiment, the ratio of unfiltered water 620 in the first sub-reservoir 612 to filtered dialysate 622 in the second sub-reservoir 614 is 30 to 70, preferably 40 to 60. The movable membrane 602 has moved toward a second side, proximate a center longitudinal plane 600c, of the reservoir bag 600 to accommodate both the unfiltered water 620 and the filtered dialysate 622.

Figure 7:
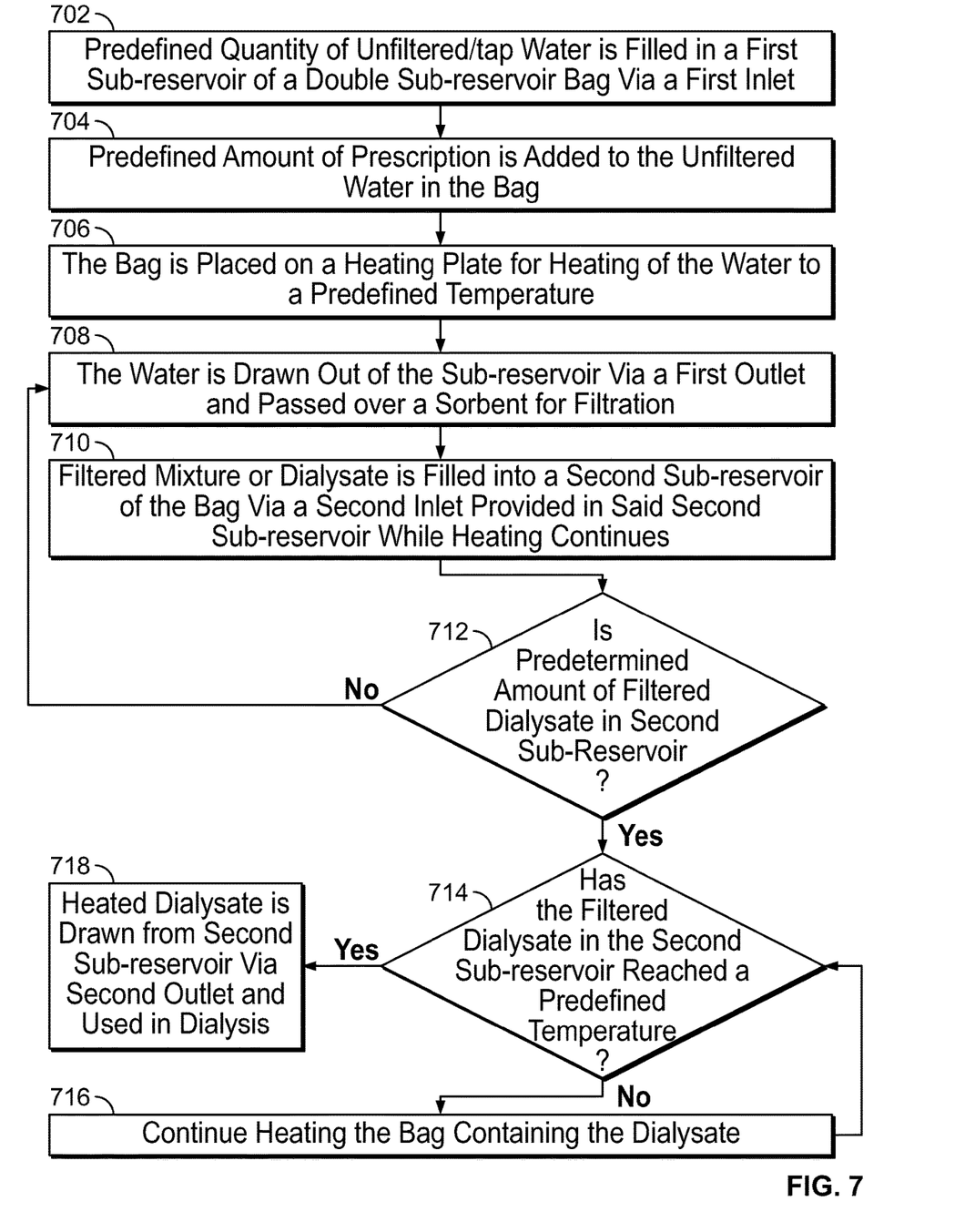
FIG. 7 is a flowchart illustrating exemplary steps of heating a dialysate by using a reservoir bag of the present specification.

FIG. 7 is a flowchart illustrating the steps of heating a dialysate by using a reservoir bag of the present specification. At step 702 a predefined quantity of unfiltered/tap water is filled in a first sub-reservoir of a double sub-reservoir bag via a first inlet provided in a wall of the first sub-reservoir. In an embodiment, 9 liters of water is filled into the first sub-reservoir. At step 704, a predefined amount of a prescription is added to the unfiltered water in the first sub-reservoir of the bag. In another embodiment, the prescription is added to the second sub-reservoir, which is empty. In an embodiment, the prescription is in a powder form, while in another embodiment, the prescription is in the form of a prescription pod or bag threaded onto an inlet of the reservoir bag. In an embodiment, the prescription may be added to the unfiltered water in the bag via the first inlet or via a third inlet. In some embodiments, said third inlet is wider than said first inlet and is accessed by opening a screw cap.

At step 706, the reservoir bag is placed on a heating plate for heating the water to a predefined temperature. At step 708, the water is drawn out of the first sub-reservoir via a first outlet provided in a wall of the first sub-reservoir of the bag and passed over a sorbent for filtration. At step 710 the filtered water or dialysate is filled into a second sub-reservoir of the bag via a second inlet provided in said second sub-reservoir as heating continues. In an embodiment, the filtered water flowing into the second reservoir mixes with the prescription added to the second sub-reservoir. In an embodiment, a pre-defined quantity of filtered water (for example, 500 mL) is added to the second sub-reservoir periodically (for example every 30 minutes). In another embodiment, filtered water is added into the second sub-reservoir as a continuous stream. Steps 708 and 710 are repeated simultaneously until it is determined at step 712 that a sufficient, predetermined amount of water or mixture has been filtered and delivered to the second sub-reservoir as dialysate. During the course of the dialysis process, the mixture from the second sub-reservoir is cycled through the dialyzer and back to the second sub-reservoir, thereby changing the chemical composition of the mixture in the second sub-reservoir as quantities of urea from the patient undergoing the dialysis treatment, as well as other chemicals from the dialyzer, get added to the second sub-reservoir. Hence, the mixture in the second sub-reservoir requires periodic or continuous dilution by addition of water obtained from the first sub-reservoir. It is determined at step 714 if the filtered dialysate contained in the second sub-reservoir has reached the predefined temperature. If not, the heating is continued at step 716. If the dialysate has reached the predefined temperature, at step 718 the dialysate is drawn from the second sub-reservoir via a second outlet in a wall of said second sub-reservoir and is used in a dialysis process. At the end of the dialysis process, the first sub-reservoir is empty and the second sub-reservoir contains approximately 12 liters of fluid which can then be discarded.

Figure 8:
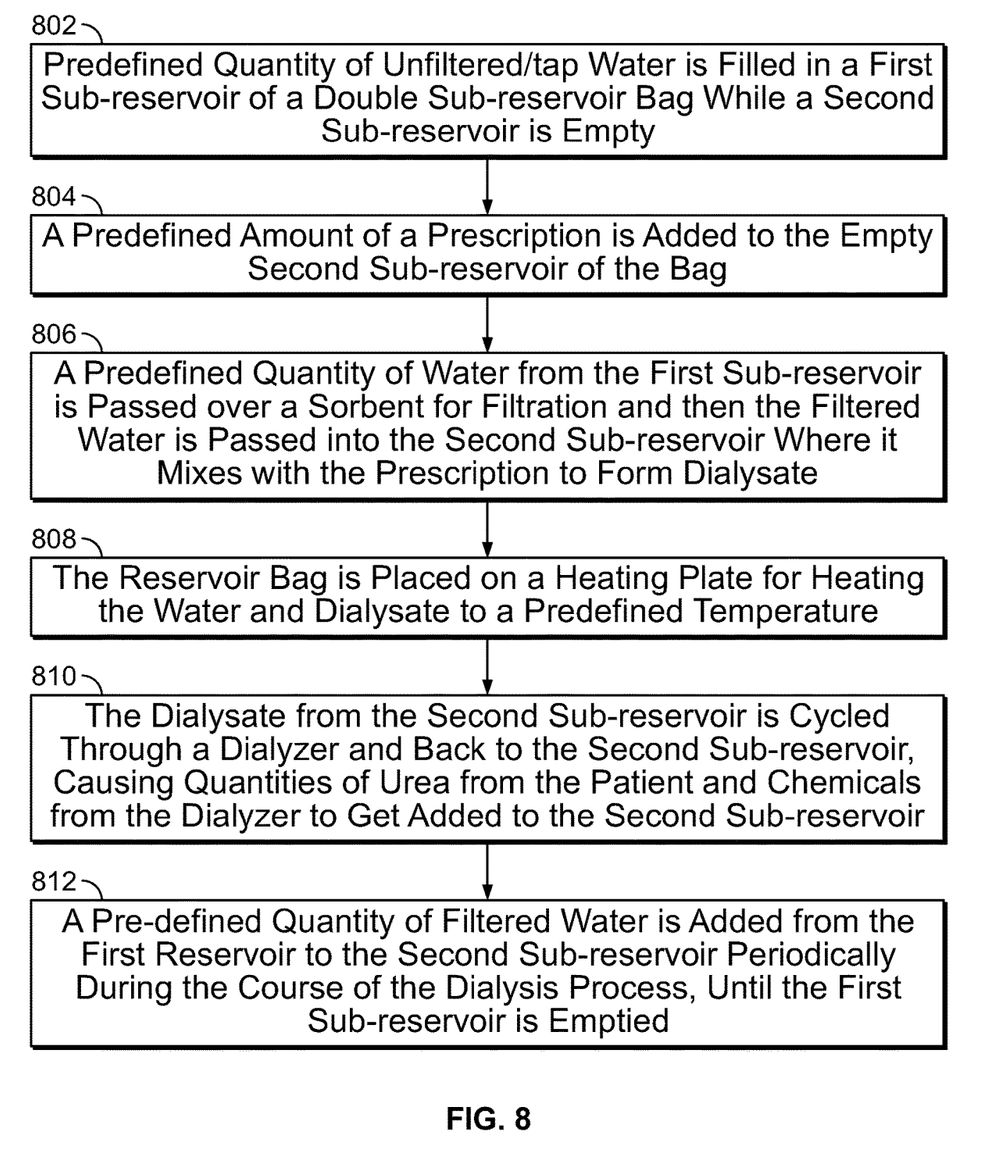
FIG. 8 is a flowchart illustrating exemplary steps of heating a dialysate by using a reservoir bag of the present specification.

FIG. 8 is a flowchart illustrating an exemplary method of performing dialysis by using the reservoir bag disclosed in the present specification. At step 802, unfiltered/tap water is filled in a first sub-reservoir of a double sub-reservoir bag while the second sub-reservoir is empty. In an embodiment, the first reservoir is filled with 9 liters of water flowing from a tap. In an embodiment, the first sub-reservoir is filled from the tap at a flow rate ranging from 200 mL/minute to 500 mL/minute, in approximately 18 to 40 minutes. At step 804, a predefined amount of a prescription is added to the empty second sub-reservoir of the bag. At step 806, a predefined quantity of water from the first sub-reservoir is passed over a sorbent for filtration, and then the filtered water is passed into the second sub-reservoir, where it mixes with the prescription to form the dialysate. In an embodiment, filling of the second sub-reservoir is begun as soon as a predefined quantity of water has been filled in the first sub-reservoir, to ensure that the first sub reservoir does not run dry. In an embodiment, initially, approximately, 6 liters of filtered water is filled into the second sub-reservoir and is mixed with the patient's prescription therein to form the dialysate, and approximately 2 liters of tap water runs through the sorbent at a time. Once 6 liters of water is filled in the first sub-reservoir, transfer of water from the first sub-reservoir to the second sub-reservoir through the sorbent begins. In embodiments, 6 liters of filtered water is filled in the second sub-reservoir via a pump operating at a flow rate ranging from 200 mL/minute to 500 mL/minute, in approximately 12 to 30 minutes. In an embodiment, steps 802 to 806 are completed in a time period ranging from approximately 18 to 32 minutes. At step 808, the reservoir bag is placed on a heating plate for heating the water and dialysate to a predefined temperature. At step 810 the dialysate from the second sub-reservoir is cycled through a dialyzer and back to the second sub-reservoir, thereby changing the chemical composition of the mixture in the second sub-reservoir as quantities of urea from the patient undergoing the dialysis treatment, as well as other chemicals from the dialyzer, are transferred to the second sub-reservoir. Hence, the mixture in the second sub-reservoir requires periodic or continuous dilution by addition of water obtained from the first sub-reservoir. In an embodiment, water is pumped into the dialyzer from the second sub-reservoir at a rate of approximately 300 ml/minute. At step 812, a pre-defined quantity of filtered water (for example, 500 mL) is added from the first reservoir to the second sub-reservoir periodically (for example every 30 minutes), until the first sub-reservoir is emptied. In an embodiment, where the first sub-reservoir is filled with 9 liters of water, of which 6 liters is initially transferred to the second sub-reservoir via a sorbent, the remaining 3 liters is transferred in small batches of 500 ml each periodically at an interval of 30 minutes during the dialysis process. At the end of the dialysis process, the first sub-reservoir is empty and the second sub-reservoir contains approximately 12 liters of fluid, of which approximately 3 liters has been received from the patient's body and the dialyzer.

The above examples are merely illustrative of the many applications of the reservoir bag of the present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A reservoir bag for containing a dialysate fluid during a dialysis treatment, wherein the reservoir bag is defined at least by a first wall and a second wall and wherein the reservoir bag comprises:
   a membrane extending from the first wall of the reservoir bag to the second wall of the reservoir bag, the second wall opposing the first wall,
   wherein the membrane is attached to the first wall and the second wall so that an internal volume of the reservoir bag is divided into a first sub-reservoir and a second sub-reservoir,
   wherein the first sub-reservoir and second sub-reservoir are fluidically isolated from each other,
   wherein the membrane is flexible such that, upon application of fluid pressure, the membrane moves causing the first sub-reservoir to have a changeable volume and the second sub-reservoir to have a changeable volume, and
   wherein a maximum volume of the first sub-reservoir is equal to 80% to 100% of an entire amount of the internal volume of the reservoir bag and a maximum volume of the second sub-reservoir is equal to 80% to 100% of the entire amount of the internal volume of the reservoir bag;
   a first inlet and a first outlet positioned on a surface of the reservoir bag for enabling fluid entry into, and exit out of, the first sub-reservoir;
   a second inlet and a second outlet positioned on a surface of the reservoir bag for enabling fluid entry into, and exit out of, the second sub-reservoir; and
   a third inlet positioned on a surface of the reservoir bag for enabling fluid entry into, and exit out of, the first sub-reservoir.

2. The reservoir bag of claim 1 wherein the first wall of the reservoir bag is defined by a first length having a first midpoint positioned along the first length and wherein the membrane has a first end attached to the first wall at the first midpoint.

3. The reservoir bag of claim 2 wherein the second wall of the reservoir bag is defined by a second length having a second midpoint along the second length and wherein the membrane has a second end attached to the second wall at the second midpoint.

4. The reservoir bag of claim 1 wherein the first sub-reservoir is adapted to receive an unfiltered mixture of water and compounds via the first inlet and adapted to be a source of the unfiltered mixture of water and compounds to a sorbent device in a dialysis machine via the first outlet.

5. The reservoir bag of claim 4 wherein the second sub-reservoir is adapted to receive a filtered mixture of water and compounds via the second inlet and adapted to be a source of the filtered mixture of water and compounds to the dialysis machine via the second outlet.

6. The reservoir bag of claim 1 wherein the membrane has a thickness that is less than a thickness of the first wall and the second wall.

7. The reservoir bag of claim 1 wherein the reservoir bag comprises one or more handles extending outside the bag for moving the bag.

8. The reservoir bag of claim 1 wherein the first wall of the reservoir bag is defined by a first length having a first midpoint positioned along the first length and a first end of the membrane is attached to the first wall at a location along the first wall that is positioned at a distance less than the distance to the first midpoint.

9. The reservoir bag of claim 8 wherein the second wall of the reservoir bag is defined by a second length having a second midpoint positioned along the second length and a second end of the membrane is attached to the second wall at a location along the second wall that is positioned at a distance less than the distance to the second midpoint.

10. A method of heating water in a reservoir bag to be used in a dialysis treatment, the reservoir bag comprising a first sub-reservoir and a second sub-reservoir, wherein the first and second sub-reservoirs are fluidically isolated, the method comprising:
    filling the first sub-reservoir with unfiltered water through a first inlet on the reservoir bag;
    applying heat to the reservoir bag to heat up the unfiltered water in the reservoir bag to a predefined temperature;
    extracting the unfiltered water out of the first sub-reservoir through a first outlet;
    passing the unfiltered water through a sorbent cartridge to generate filtered water;
    filling the filtered water into the second sub-reservoir through a second inlet;
    determining a temperature of the filtered water in the reservoir bag; and
    terminating heating the reservoir bag when the filtered water has a predefined temperature.

11. The method of claim 10 further comprising adding a plurality of compounds to the unfiltered water through the first inlet.

12. The method of claim 10 wherein the reservoir bag comprises a membrane extending from a first wall of the reservoir bag to a second opposing wall of the reservoir bag, wherein the membrane is attached to the first wall and the second wall so that an internal volume of the reservoir bag is divided into the first sub-reservoir and the second sub-reservoir.

13. The method of claim 12 wherein the membrane is flexible such that, upon application of fluid pressure, the membrane moves causing the first sub-reservoir to have a changeable volume and the second sub-reservoir to have a changeable volume.

14. The method of claim 13 wherein a maximum volume of the first sub-reservoir is equal to 80-100% of the internal volume of the reservoir bag and a maximum volume of the second sub-reservoir is equal to 80-100% of the internal volume of the reservoir bag.

15. The method of claim 13 wherein the first inlet and the first outlet are positioned on a surface of the reservoir bag for enabling fluid entry into, and exit out of, the first sub-reservoir and the second inlet is positioned on a surface of the reservoir bag for enabling fluid entry into, and exit out of, the second sub-reservoir.

16. The method of claim 10 wherein, when the dialysis treatment is initiated, the reservoir bag contains a first volume of fluid, wherein the first sub-reservoir contains a first portion of the first volume of fluid and the second sub-reservoir comprises a second portion of the first volume of fluid, wherein the second portion is equal to 0 to 10% of the first portion.

17. The method of claim 16 wherein, after a priming procedure, the first sub-reservoir contains 10-40% of the first volume of fluid and the second sub-reservoir comprises between 20-70% of the first volume of fluid.

18. The method of claim 16 further comprising periodically performing a plurality of dilutions during the dialysis treatment by passing water from the first sub-reservoir to the second sub-reservoir.

19. The method of claim 18 wherein, after a first dilution of the plurality of dilutions, the first sub-reservoir contains 5-35% of the first volume of fluid and the second sub-reservoir comprises between 40-80% of the first volume of fluid.

20. The method of claim 19 wherein, after a second dilution of the plurality of dilutions, the first sub-reservoir contains 0-30% of the first volume of fluid and the second sub-reservoir comprises between 50-90% of the first volume of fluid.

21. The method of claim 20 wherein, after a third dilution of the plurality of dilutions, the first sub-reservoir contains 0-25% of the first volume of fluid and the second sub-reservoir comprises between 60-100% of the first volume of fluid.

22. The method of claim 21 wherein, after a fourth dilution of the plurality of dilutions, the first sub-reservoir contains 0-15% of the first volume of fluid and the second sub-reservoir comprises between 70-110% of the first volume of fluid.

23. The method of claim 22 wherein, after a fifth dilution of the plurality of dilutions, the first sub-reservoir contains 0-15% of the first volume of fluid and the second sub-reservoir comprises between 80-120% of the first volume of fluid.

24. The method of claim 23 wherein, after a sixth dilution of the plurality of dilutions, the first sub-reservoir contains 0-10% of the first volume of fluid and the second sub-reservoir comprises between 90-130% of the first volume of fluid.

25. The method of claim 24 wherein, at an end of the dialysis treatment, the first sub-reservoir contains 0-10% of the first volume of fluid and the second sub-reservoir comprises between 100-140% of the first volume of fluid.

* * * * *